United States Patent [19]

Foguet et al.

[11] Patent Number: 4,603,134

[45] Date of Patent: Jul. 29, 1986

[54] PIPERAZINE DERIVATIVE AND PHARMACEUTICAL COMPOSITION CONTAINING THE SAME

[75] Inventors: Rafael Foguet; Santiago Gubert; Manuel Raga; Aurelio Sacristän; José A. Ortiz, all of Barcelona, Spain

[73] Assignee: Ferrer International, S.A., Barcelona, Spain

[21] Appl. No.: 690,973

[22] Filed: Jan. 11, 1985

[30] Foreign Application Priority Data

Jan. 17, 1984 [ES] Spain .................................... 529.395

[51] Int. Cl.⁴ .................. A61K 31/495; C07D 405/06
[52] U.S. Cl. .................................... 514/252; 544/374; 544/396; 549/455
[58] Field of Search .......................... 544/374; 514/252

[56] References Cited

U.S. PATENT DOCUMENTS 3,966,735  6/1976  Milkowski et al. ................. 544/374

Primary Examiner—Glennon H. Hollrah
Assistant Examiner—James H. Turnipseed
Attorney, Agent, or Firm—Michael J. Striker

[57] ABSTRACT

A piperazine derivative is disclosed of formula (I):

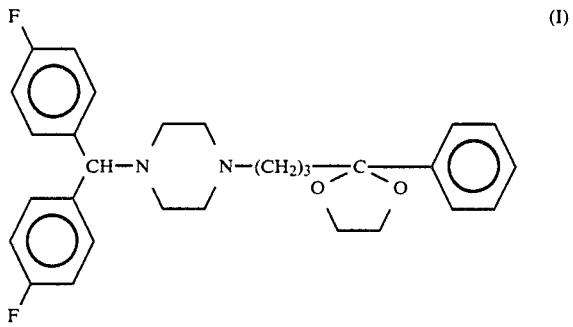

and the non-toxic addition salts thereof, along with a process for preparation, pharmaceutical composition, and method of treating conditions characterized by histamine activity.

4 Claims, No Drawings

PIPERAZINE DERIVATIVE AND PHARMACEUTICAL COMPOSITION CONTAINING THE SAME

BACKGROUND OF THE INVENTION

The present invention relates to a piperazine derivative of the formula (I):

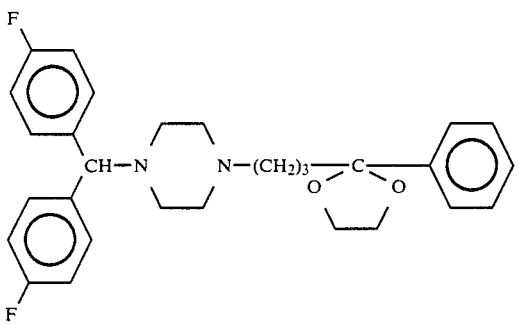

and the non-toxic addition salts thereof.

The non-fluorine analog, described in Spanish Pat. No. 514 340, is a useful vasoactive antiarrhythmic and hypertensor agent. However, its anti-histaminic effect is unsatisfactory.

SUMMARY OF THE INVENTION

The compound of the present invention may be prepared according to the following scheme:

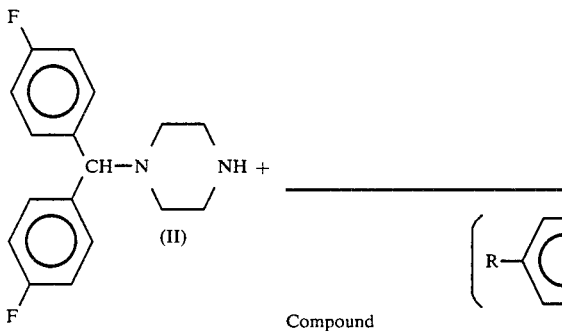

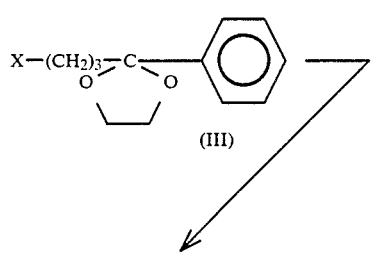

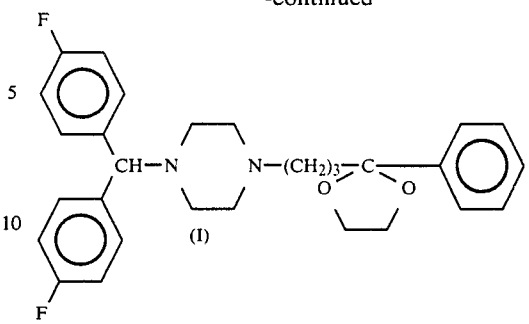

ps wherein X, in the starting compound of the general formula (III), is chlorine or bromine.

The reaction between N-mono-(4,4'-difluorobenzhydryl)piperazine (II) and 2-(3-halopropyl)-2-phenyl-1,3-dioxolane (III) is conveniently carried out in a medium composed of an alkanol having from 1 to 4 carbon atoms, preferably ethanol, and in the presence of a base selected from an alkaline/alkaline earth carbonate or bicarbonate, preferably sodium bicarbonate, under reflux. If desired, the non-toxic addition salts are obtained by treating with an acid, preferably dissolved in an alkanol having from 1 to 4 carbon atoms, such as methanol, ethanol or isopropanol.

The compound of the present invention, like its non-fluorine analog, described in Spanish Pat. No. 514 340 displays strong activity on the blood stream, and thus is a useful vasoactive, antiarrhythmic and hypotensor agent. Moreover, the compound, according to the present invention, has proven to possess an additional anti-histaminic effect, higher than that of its non-fluorine analog. In Table 1, the parameter of anti-histamine activity, expressed as $ED_{50}$ (mol/liter), is comparatively tabulated for the compound of formula (I) as well as its analog (Spanish Pat. No. 514 340) versus Cinnarizine and Flunarizine.

TABLE 1

| Compound | | $ED_{50}$ (mol/liter) |
|---|---|---|
| Example 1 | R = F | $1.5 \times 10^{-7}$ |
| Spanish Pat. 514 340 | R = H | $3.5 \times 10^{-7}$ |
| Cinnarizine | — | $1.7 \times 10^{-7}$ |
| Flunarizine | — | $2.7 \times 10^{-7}$ |

The anti-histamine activity was tested in an isolate of guinea-pig ileum, suspended in a Tyrode bath at 32°–35° C. according to a protocol described by R. A. Turner (Screening Methods in Pharmacology, Academic Press, 1965, p. 43).

The compound of the present invention and the non-toxic addition salts thereof, mixed with pharmaceutically acceptable carriers, can be administered by the oral route in the form of tablets, capsules, syrup, solution, etc., by injection route and by rectal route, at daily doses ranging from 50 to 500 mg.

The novel features which are considered characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

EXAMPLE 1

1-(4,4'-difluorobenzhydryl)-4-(2-phenyl-1,3-dioxolane-2-propyl)piperazine 14 g of N-mono-(4,4'-difluorobenzhydryl)piperzine (0.049 mol) are dissolved in 200 ml of absolute ethanol in the presence of 5.88 g of sodium bicarbonate (0.07 mol). The resulting mixture is gently treated with 13.3 g solution of 2-(3-chloropropyl)-2-phenyl-1,3-dioxolane (0.059 mol) in 50 ml of absolute ethanol, and then refluxed for 24 hours. After conditioning the reaction mass, it is filtered off and the ethanol is removed by distillation at vacuum. The residue, dissolved in n-hexane, is subjected to silicagel column chromatography (1-hour activation at 120° C.) with a mixture of n-hexane and acetone used as eluent. The eluate is concentrated until dryness, and the obtained oil crystallizes form n-hexane, yielding 9.2 g of crystals of 1-(4,4'-difluorobenzhydryl)-4-(2-phenyl-1,3-dioxolane-2-propyl)piperazine.

Yield: 39%. M.P. 76°–78° C. (d). IR (KBr), cm$^{-1}$: 3000–2800, 1600, 1500, 1230, 1010, 840–830, 780, 910.

EXAMPLE 2

1-(4,4'-difluorobenzhydryl)-4-(2-phenyl-1,3-dioxolane-2-propyl)piperazine maleate 11 g of 1-(4,4'-difluorobenzhydryl)-4-(2-phenyl-1,3-dioxolane-2-propyl)piperazine are dissolved in 250 ml of absolute ethanol, and then treated with 1M maleic acid ethanol solution up to pH=4.0. The mixture is left to crystallize in a refrigerator, yielding 8.3 g of crystals of 1-(4,4'-difluorobenzhydryl)-4-(2-phenyl-1,3-dioxolane-2-propyl)piperzine.

Yield: 61%. M.p.: 190°–193° C. IR(KBr), cm$^{-1}$: 3000–2400, 1700, 1600, 1575, 1350, 1220, 870, 830, 700.

It will be understood that each of the elements described above, or two or more together, may also find a useful application in other types of pharmaceutical compositions differing from the types described above.

While the invention has been illustrated and described as embodied in piperazine derivatives, process for the production thereof, and pharmaceutical composition containing the same, it is not intended to to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. Piperazine derivative of the formula (I):

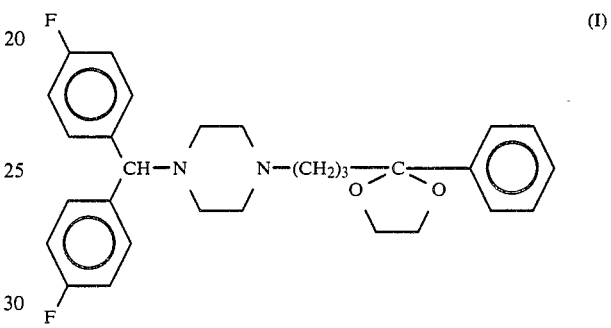

and the non-toxic addition salts thereof.

2. Method of treating conditions characterized by histamine activity, comprising the step of:
   administering, in an effective amount, an anti-histamine composition comprising the compound according to claim 1 in combination with a pharmaceutically acceptable carrier means.

3. The method according to claim 2, wherein said anti-histamine effective amount comprises a daily dose of 50 to 500 mg of said compound.

4. The method according to claim 2, wherein said administering comprises oral, injection or rectal route administering.